(12) United States Patent
Bonda

(10) Patent No.: US 7,776,614 B2
(45) Date of Patent: Aug. 17, 2010

(54) TEST METHOD FOR DETERMINING COMPOUNDS CAPABLE OF QUENCHING ELECTRONIC SINGLET STATE EXCITATION OF PHOTOACTIVE COMPOUNDS

(75) Inventor: Craig A. Bonda, Winfield, IL (US)

(73) Assignee: Hallstar Innovations Corp., Chicago, IL (US)

( * ) Notice: Subject to any disclaimer, the term of this patent is extended or adjusted under 35 U.S.C. 154(b) by 198 days.

(21) Appl. No.: 11/891,280

(22) Filed: Aug. 9, 2007

(65) Prior Publication Data
US 2009/0042312 A1    Feb. 12, 2009

(51) Int. Cl.
*G01N 21/76*    (2006.01)
(52) U.S. Cl. .................. 436/172; 436/176; 252/301; 252/500; 252/601; 424/60; 424/407; 424/459
(58) Field of Classification Search .......... 436/172, 436/176
See application file for complete search history.

(56) References Cited

U.S. PATENT DOCUMENTS

| | | | | |
|---|---|---|---|---|
| 4,293,542 | A | * | 10/1981 | Lang et al. ............ 424/47 |
| 4,307,240 | A | | 12/1981 | Ching |
| 4,562,278 | A | | 12/1985 | Hill |
| 5,576,354 | A | | 11/1996 | Deflandre et al. |
| 5,989,528 | A | | 11/1999 | Tanner et al. |
| 5,993,789 | A | * | 11/1999 | Bonda et al. ............ 424/59 |
| 6,113,931 | A | | 9/2000 | Bonda et al. |
| 6,225,052 | B1 | * | 5/2001 | Batz et al. ............ 435/6 |
| 6,284,916 | B1 | | 9/2001 | Bonda et al. |
| 6,485,713 | B1 | | 11/2002 | Bonda et al. |
| 6,518,451 | B2 | | 2/2003 | Bonda et al. |

(Continued)

FOREIGN PATENT DOCUMENTS

SU    1273360    11/1986

(Continued)

OTHER PUBLICATIONS

Min et al., "Spectroscopic studies on the interaction of cinnamic acid and its hydroxyl derivatives with human serum albumin", Journal of Molecular Structure, vol. 692, pp. 71-80 (Mar. 2004).*

(Continued)

*Primary Examiner*—Vickie Kim
*Assistant Examiner*—Dirk Bass
(74) *Attorney, Agent, or Firm*—Marshall, Gerstein & Borun LLP

(57) ABSTRACT

A method of testing a compound for its capability of quenching singlet excited state energy from a photon-excited photoactive compound, thereby photostabilizing said photoactive compound, comprising mixing: (1) a composition comprising a photoactive compound in a solvent and determining the degree of fluorescence of said composition (1) by exposing the composition (1) to UV radiation in an amount sufficient for the photoactive compound to reach an electronic singlet excited state, and (2) a mixture comprising said photoactive compound with a test compound in a solvent, and determining the degree of fluorescence of said mixture (2) by exposing the mixture to UV radiation to the same degree as composition (1), and comparing the degree of fluorescence of composition (1) with mixture (2).

18 Claims, 15 Drawing Sheets
(3 of 15 Drawing Sheet(s) Filed in Color)

U.S. PATENT DOCUMENTS

| | | | |
|---|---|---|---|
| 6,537,529 | B1 | 3/2003 | Bonda |
| 6,551,605 | B2 | 4/2003 | Bonda |
| 6,800,274 | B2 | 10/2004 | Bonda et al. |
| 6,919,473 | B2 | 7/2005 | Bonda et al. |
| 6,962,692 | B2 | 11/2005 | Bonda et al. |
| 7,064,114 | B2 * | 6/2006 | Yiv et al. ................. 514/54 |
| 7,235,587 | B2 | 6/2007 | Bonda et al. |
| 7,449,698 | B2 * | 11/2008 | Nguyen et al. .......... 250/484.4 |
| 2002/0127192 | A1 * | 9/2002 | Murphy et al. ................ 424/64 |
| 2004/0047817 | A1 | 3/2004 | Bonda |
| 2004/0047818 | A1 | 3/2004 | Bonda |
| 2004/0170579 | A1 | 9/2004 | Mobius |
| 2005/0191249 | A1 | 9/2005 | Bonda et al. |
| 2006/0002869 | A1 | 1/2006 | Bonda et al. |

FOREIGN PATENT DOCUMENTS

| | | |
|---|---|---|
| WO | WO-0242368 | 5/2002 |
| WO | WO 2007128840 A2 * | 11/2007 |

OTHER PUBLICATIONS

Horiba Jobin Yvon Ltd., A Guide to Recording Fluorescence Quantum Yields, www.jyhoriba.co.uk.

International Search Report for PCT/US2008/058456 dated Jun. 27, 2008.

Written Opinion for PCT/US2008/058456 dated Jun. 27, 2008.

N. G. Senchenya, et al., *Silicon-containing esters of α-cyanoacrylic acid: synthesis and properties*, Russian Chemical Bulletin, vol. 42, No. 5, May 1993, pp. 909-11.

International Search Report for PCT/US/2008/058454, dated Sep. 23, 2008.

Written Opinion of the International Searching Authority for PCT/US/2008/058454, dated Sep. 23, 2008.

Baussard, Jean-Francois, "Chap. II: Donor-Acceptor pairs for Forster Resonance Energy Transfer (FRET):" in Synthesis of New Ionic Functional Polymers by Free Radical Polymerization via the RAFT Process, Dissertation, Catholic University of Louvain, Jan. 26, 2004.

Somsen et. al., "Planar chromatography coupled with spectroscopic techniques" in J. Chromatography A, vol. 703, 613-65 (1995).

* cited by examiner

TEST METHOD FOR DETERMINING COMPOUNDS CAPABLE OF QUENCHING ELECTRONIC SINGLET STATE EXCITATION OF PHOTOACTIVE COMPOUNDS

FIELD OF THE INVENTION

The present invention is directed to a test method for determining compounds capable of quenching electronic singlet state excitation of photoactive compounds or quenching electronic excited state(s) of chromophore-containing UV-absorbing organic molecules in photoactive compositions. More particularly, it has been found that by mixing a chromophore-containing UV-absorbing organic molecule, that is subject to photodegradation and that exhibits eye-visible fluorescence, with a test compound that may be capable of photostabilizing the UV absorbing molecule, and observing or otherwise quantitizing the fluorescence of the UV absorber subjected to UV radiation sufficient for the UV-absorber to reach an electronic singlet excited state, before and after mixing with the test compound, photostabilization of the UV-absorber by the test compound can be determined.

BACKGROUND

The absorption of ultraviolet light by a chromophore-containing organic molecule causes the excitation of an electron in the chromophore moiety from an initially occupied, low energy orbital to a high energy, previously unoccupied orbital. The energy of the absorbed photon is used to energize an electron and cause it to "jump" to a higher energy orbital, see Turro, Modern Molecular Photochemistry, 1991. Two excited electronic states derive from the electronic orbital configuration produced by UV light absorption. In one state, the electron spins are paired (antiparallel) and in the other state the electron spins are unpaired (parallel). The state with paired spins has no resultant spin magnetic moment, but the state with unpaired spins possesses a net spin magnetic moment. A state with paired spins remains a single state in the presence of a magnetic field, and is termed a singlet state. A state with unpaired spins interacts with a magnetic field and splits into three quantized states, and is termed a triplet state.

In the electronically excited state, the chromophore-containing organic molecule is prone to degrade via a number of known pathways and, therefore, can absorb little or no additional UV light. In order to photostabilize an electronically excited chromophore-containing organic molecule in order to provide sufficient UV protection, it must be returned to the ground state before it degrades.

As stated in this assignees pending applications, Ser. Nos. 10/241,388; 10/361,223; and 10/7865,793, an α-cyano-β,β-diphenylacrylate compound (e.g., octocrylene) is known to quench (accept) the excited triplet state energy of an excited photoactive compound by dissipating the energy kinetically in the form of rapid isomerizations. This process is shown below:

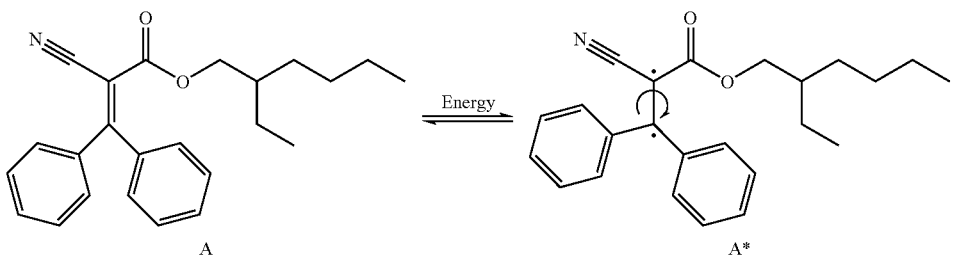

wherein the α-cyano-β,β-diphenylacrylate compound (octocrylene shown above as structure A), accepts the triplet excited state energy from a photoactive compound and forms a diradical (shown above as structure A*) at the α and β positions of the acrylate, which converts the double bond into a single bond and allows for the free rotation of the phenyl groups. This rotation occurs rapidly and efficiently to dissipate any excited triplet state energy accepted by the α-cyano-β,β-diphenylacrylate compound from the photoactive compound.

While octocrylene is able to quench (accept) the triplet excited state energy from a photoactive compound, thereby photostabilizing, to some degree, dibenzoylmethane derivatives, as shown in examples 1, 4, 6 and 8 of Deflandre et al. U.S. Pat. No. 5,576,354, there exists a need in the photoactive composition art to provide a simple test indicative of the capability of a compound to quench (accept) the singlet excited state energy from photoactive compounds, particularly UV-absorbing compounds.

A photoactive compound can be considered photostable when, for example, after 30 MED irradiation the photoactive compound has retained at least about 90% of its original absorbance at a wavelength, or over a range of wavelengths of interest (e.g., the wavelength at which a photoactive compound has a peak absorbance, such as 350-370 nm for avobenzone). Likewise, a sunscreen composition can include a plurality of photoactive compounds and a sunscreen composition, as a whole, can be considered stable when, for example, after 30 MED irradiation the sunscreen composition has retained at least about 90% of its original absorbance at one or more wavelengths of interest (e.g., at or near the peak absorbance wavelength of the primary photoactive compound). The absorbance testing is tedious and time consuming. In accordance with the test methods described herein, photostabilizing (singlet excited state energy-accepting) compounds can be found using a visual fluorescence test.

SUMMARY

The test method described herein is a simple, inexpensive method that determines whether a test compound, mixed with a UV absorbing compound, photostabilizes the UV-absorbing compound based on the ability of the test compound to quench fluorescence of the UV-absorbing compound. UV-absorbing compounds that are contacted by UV radiation (about 290 nm to about 400 nm) will reach an elecronically excited singlet state, and many of the UV compounds in the singlet excited state will exhibit visually recongnizable (or machine-readable) fluorescence when viewed in dark surroundings. When the UV-absorbing compound is mixed with a test compound that is found to quench (accept) the singlet excited energy of the electronically excited UV-absorbing compound, the fluorescence of the electronically excited UV-absorbing compound will be markedly and visually decreased when viewed in the same dark environment or analyzed by a device capable of quantitizing fluorescence.

In accordance with the present invention, it is possible to easily and quickly test and compound for its ability to quench (accept) the electronically excited singlet state energy from any UV-absorbing organic molecule by visually comparing the degree of fluorescence observed in (1) the excited UV-absorbing organic molecule in a solvent, compared to (2) a combination of the UV-absorbing compound mixed with the test, potentially quenching, organic molecule in the same solvent, each subjected to the same quantity of UV radiation. Any decrease in the fluorescence of the combination ((2) above) compared to the fluorescence of the UV-absorber ((1) above) indicates that the test molecule is capable of quenching (accepting) the electronically excited singlet state energy from, and thereby photostabilize, the UV-absorbing molecule. The larger the observed or machine-quantitized difference in fluorescence, the greater the excited singlet state quenching ability of the test compound.

DETAILED DESCRIPTION OF THE PREFERRED EMBODIMENTS

Figure 1:
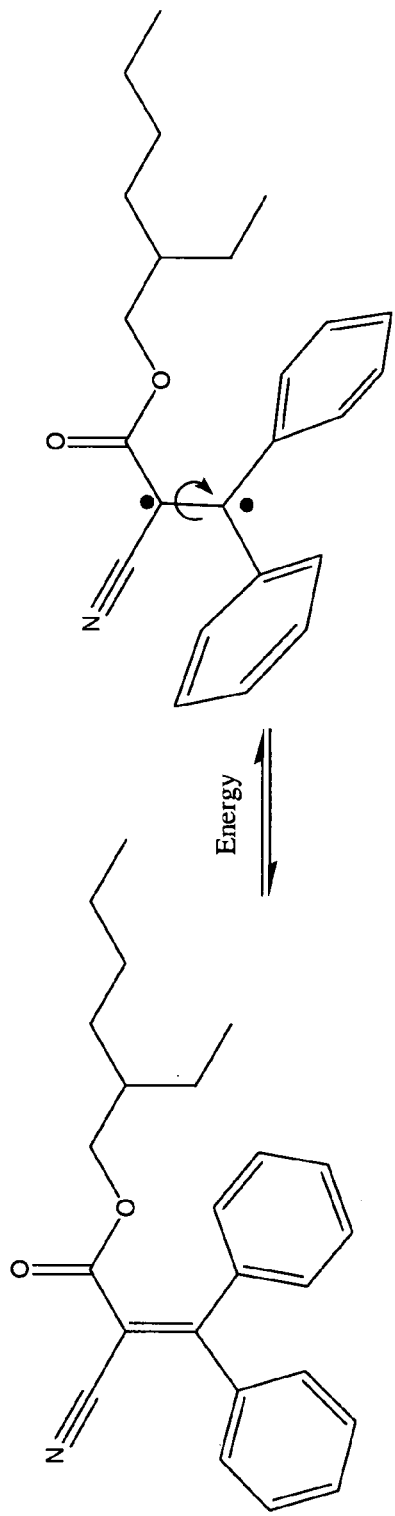
FIG. 1 is a structural representation of the isomerization of Octocrylene which occurs following excitation of Octocrylene either by photon absorbance or as the result of accepting (quenching) the excited triplet state energy of an excited photoactive compound.

The patent or application file contains at least one drawing executed in color. Copies of this patent or patent application publication with color drawing(s) will be provided by the Office upon request and payment of the necessary fee.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The term "cyano" as used herein refers to a —C≡N group, also designated —CN.

Photoactive compositions, e.g., sunscreen compositions, generally include UV-A and UV-B photoactive compounds in a cosmetically acceptable carrier, optionally including additives, such as emollients, stabilizers, emulsifiers, and combinations thereof. These additives can be used in preparing a UV filter composition in an emulsion (oil-in-water or water-in-oil) from a composition that includes one or more photoactive compounds and a solvent or a solvent combination that includes one or more organic solvents and water. When made, preferably the emulsion is an oil-in-water emulsion, wherein the oil phase is primarily formed from a mixture of the UV filter compound(s) and one or more organic solvents.

A typical photoactive composition includes one or more photoactive compounds, wherein the photoactive compound(s) act to absorb UV radiation and thereby protect the substrate (e.g., human skin, resins, films, and the like) from the harmful effects of UV radiation. The absorption process causes a photoactive compound to reach an excited state, wherein the excited state is characterized by the presence of excited electronic energy (e.g., singlet state energy or triplet state energy), as compared to the ground state of the photoactive compound. Once a photoactive compound reaches an excited state there exists a number of pathways by which the excited photoactive compound can dissipate its excess energy (e.g., singlet and/or triplet energy), however, some of those pathways adversely affect the ability of the photoactive compound to further absorb UV radiation.

A photoactive compound is one that responds to light photoelectrically. In the methods of photostabilization disclosed herein, a photoactive compound is one that responds to UV radiation photoelectrically. For example, all photoactive compound-containing compositions that respond to UV radiation photoelectrically by photoactive compound photodegradation benefit highly by the inclusion of a singlet state quenching compound that can be easily and quickly found by the test methods described herein. Photostability is a problem with all UV filters because they all reach an electronic singlet excited state upon exposure to UV radiation.

UV filters can be photostabilized by the singlet state quenching molecules that can be easily and quickly found by the test methods described herein. The UV filters that benefit in photostabilization by singlet excited state quenching molecules include all of the following, including combinations of any two or more, and include compounds selected from the following categories (with specific examples) including: p-aminobenzoic acid, its salts and its derivatives (ethyl, isobutyl, glyceryl esters; p-dimethylaminobenzoic acid); anthranilates (o-aminobenzoates; methyl, menthyl, phenyl, benzyl, phenylethyl, linalyl, terpinyl, and cyclohexenyl esters); salicylates (octyl, amyl, phenyl, benzyl, menthyl (homosalate), glyceryl, and dipropyleneglycol esters); cinnamic acid derivatives (menthyl and benzyl esters, alpha-phenyl cinnamonitrile; butyl cinnamoyl pyruvate); dihydroxycinnamic acid derivatives (umbelliferone, methylumbelliferone, methylaceto-umbelliferone); trihydroxycinnamic acid derivatives (esculetin, methylesculetin, daphnetin, and the glucosides, esculin and daphnin); hydrocarbons (diphenylbutadiene, stilbene); dibenzalacetone; benzalacetophenone; naphtholsulfonates (sodium salts of 2-naphthol-3,6-disulfonic and of 2-naphthol-6,8-disulfonic acids); dihydroxynaphthoic acid and its salts; o- and p-hydroxydiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric acid derivatives; vilouric acid derivatives; tannic acid and its derivatives; hydroquinone; esters and polyesters of naphthalene dicarboxylic acid; 4-isopropyldibenzoylmethane, butylmethoxydibenzoylmethane, and 4-isopropyl-dibenzoylmethane).

Particular UV filters that suffer from photodegradation and benefit from electronically excited singlet state energy quenching molecules found by the test methods described herein include: 2-ethylhexyl p-methoxycinnamate, isoamyl methoxycinnamate, 4,4'-t-butyl methoxydibenzoylmethane, octyldimethyl p-aminobenzoic acid, ethyl 4-[bis(hydroxypropyl)]aminobenzoate, 2-ethylhexyl salicylate, glycerol p-aminobenzoate, 3,3,5-trimethylcyclohexyl salicylate, p-dimethylaminobenzoic acid or aminobenzoate, 2-ethylhexyl p-dimethylaminobenzoate, and combinations thereof.

The preferred UV-B photoactive compounds capable of being photostabilized with electronically excited singlet state quenching molecules found by the test methods described herein include a photoactive compound selected from the group consisting of p-aminobenzoic acid and salts and derivatives thereof; dibenzoylmethane and derivatives thereof; salicylate and derivatives thereof; cinnamic acid and derivatives thereof; dihydroxycinnamic acid and derivatives thereof; trihydroxycinnamic acid and derivatives thereof; dibenzalacetone naphtholsulfonate and salts and derivatives thereof; benzalacetophenone naphtholsulfonate and salts and derivatives thereof; dihydroxy-naphthoic acid and salts thereof; naphthalates and salts thereof, and combinations of the foregoing.

The preferred UV-A (about 320 nm to about 400 nm) photoactive compounds capable of being photostabilized with electronically excited singlet excited state quenching molecules found by the test methods described herein include a dibenzoylmethane derivative UV-A photoactive compound. Preferred dibenzoylmethane derivatives include, 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane, and combinations thereof.

All of the above described UV filters are commercially available. For example, suitable commercially available organic UV filters are identified by trade name and supplier in Table I below:

TABLE I

| CTFA Name | Trade Name | Supplier |
|---|---|---|
| benzophenone-3 | UVINUL M-40 | BASF Chemical Co. |
| benzophenone-4 | UVINUL MS-40 | BASF Chemical Co. |
| benzophenone-8 | SPECTRA-SORB UV-24 | American Cyanamid |
| DEA-methoxycinnamate | BERNEL HYDRO | Bernel Chemical |
| diethylamino hydroxybenzoyl hexyl benzoate | UVINUL A-PLUS | BASF Chemical Co. |
| diethylhexyl butamido triazone | UVISORB HEB | 3V-Sigma |
| disodium phenyl dibenzylimidazole | NEO HELIOPAN AP | Symrise |
| ethyl dihydroxypropyl-PABA | AMERSCREEN P | Amerchol Corp. |
| glyceryl PABA | NIPA G.M.P.A. | Nipa Labs. |
| homosalate | KEMESTER HMS | Humko Chemical |
| menthyl anthranilate | SUNAROME UVA | Felton Worldwide |
| octocrylene | UVINUL N-539 | BASF Chemical Co. |
| octyl dimethyl PABA | AMERSCOL | Amerchol Corp. |
| octyl methoxycinnamate | PARSOL MCX | Bernel Chemical |
| PABA | PABA | National Starch |
| 2-phenylbenzimidazole-5-sulphonic acid | EUSOLEX 6300 | EM Industries |
| TEA salicylate | SUNAROME W | Felton Worldwide |
| 2-(4-methylbenzildene)-camphor | EUSOLEX 6300 | EM Industries |
| benzophenone-1 | UVINUL 400 | BASF Chemical Co. |
| benzophenone-2 | UVINUL D-50 | BASF Chemical Co. |
| benzophenone-6 | UVINUL D-49 | BASF Chemical Co. |
| benzophenone-12 | UVINUL 408 | BASF Chemical Co. |
| 4-isopropyl dibenzoyl methane | EUSOLEX 8020 | EM Industries |
| butyl methoxy dibenzoyl methane | PARSOL 1789 | Givaudan Corp. |
| etocrylene | UVINUL N-35 | BASF Chemical Co. |
| methylene bisbenzotriazolyl tetramethylbutylphenol | TINOSORB M | Ciba Specialty Chemicals |
| bisethylhexyloxyphenol methoxyphenyl triazine. | TINOSORB S | Ciba Specialty Chemicals |

Preferred Embodiment

Qualitative Method for Screening Potential Singlet Excited State Energy—Quenching Compounds

Abbreviations

PEB—Phenylethyl benzoate

EtAc—Ethyl acetate

Q.S.—Quantity sufficient

I. Materials
  a Flexible Plates for TLC (Catalog #4420221, Whatman)
  b Pipette tips (Finntip 250 Universal, Sigma)
  c Ethyl acetate (HPLC Grade, Aldrich)
  d Phenylethyl benzoate (X-tend 226, ISP)
  e UV-absorbing and fluorescing compounds (as supplied by various manufacturers)
  f Potential fluorescence-quenching compounds (as supplied)

II. Equipment
  a Pipettor (Justor 1100DG [set to dispense 10 µl])
  b 30 ml glass beakers
  c Longwave (365 nm) UV light source (Model ENF-240C, Spectroline)

III. Procedure
  a Preparing solutions
    i NEGATIVE CONTROL I: To glass beaker, add 1 gram each of UV-absorbing and fluorescing compound and PEB. Q.S. to 10 grams with EtAc. Stir until solution is clear.
    ii NEGATIVE CONTROL II: To glass beaker, add 1 gram of UV-absorbing and fluorescing compound and 1.5 grams PEB. Q.S. to 10 grams with EtAc. Stir until solution is clear.
    iii NEGATIVE CONTROL III: To glass beaker, add 1 gram of UV-absorbing and fluorescing compound and 2 grams PEB. Q.S. to 10 grams with EtAc. Stir until solution is clear.
    iv TEST SOLUTION I: To glass beaker, add 1 gram each of UV-absorbing and fluorescing compound and PEB. Add ½ gram of potential fluorescence-quenching compound. Q.S. to 10 grams with EtAc. Stir until solution is clear.
    v TEST SOLUTION II: To glass beaker, add 1 gram each of UV-absorbing and fluorescing compound and PEB. Add 1 gram of potential fluorescence-quenching compound. Q.S. to 10 grams with EtAc. Stir until solution is clear.
  b Preparing the TLC (thin layer chromatography) plate
    i Cut 20×20 cm TLC plate into as many smaller plates as required. A convenient size is 7×4.5 cm.
    ii Starting on the left side, either above or below the centerline, dispense 10 µl of NEGATIVE CONTROL I onto the TLC plate. A round spot will appear and will almost immediately start to dry. Moving across the TLC plate and spacing evenly, repeat for NEGATIVE CONTROLS II AND III.
    iii Immediately above or below the spots for NEGATIVE CONTROLS II and III respectively, dispense 10 µl of TEST SOLUTIONS I and II. (Dispense TEST SOLUTION I immediately above or below NEGATIVE CONTROL II, and TEST COLUTION II immediately above or below NEGATIVE CONTROL III.)
    iv Allow all spots to dry for at least five minutes.

IV. Reading the Results
  a Turn on the longwave UV lamp. Place the spotted TLC plate so that the entire plate is evenly illuminated. The spots representing NEGATIVE CONTROLS I, II, and III should be fluorescing with graduated intensities (I>II>III).
  b Compare the spots representing TEST SOLUTIONS I and II with each other. TEST SOLUTION I should be at least somewhat brighter than TEST SOLUTION II.
  c Now compare TEST SOLUTIONS I and II with NEGATIVE CONTOLS II and III. If TEST SOLUTIONS I and II have the same or very similar fluorescence intensities as the corresponding NEGATIVE CONTROLS, then the test compound is not quenching the fluorescence of the UV-absorbing and fluorescing compound.
  d If the spots representing TEST SOLUTIONS I and II are fluorescing with significantly less intensities than the corresponding NEGATIVE CONTROLS, then the test compound probably is quenching the fluorescence of the UV-absorbing and fluorescing compound, though other explanations for this observation are possible and should be ruled out.

In accordance with another embodiment of finding suitable electronically excited singlet energy-quenching compounds for photodegradable UV-absorbing compounds, the fluorescence emission spectra of the photodegradable UV-absorbing compound is compared to the fluorescence absorption spectra of the potentially UV-absorbing (quenching) compound. In accordance with this embodiment, the more the two spectra overlap, the more photostabilization will be provided by the potential singlet energy-quenching compound. Since particular solvents will skew the fluorescence absorption and fluorescence emission spectra, the comparisons (fluorescence absorption and fluorescence emission spectra) preferably should be carried out in the same solvent or combination of solvents Useful results, however, also can be obtained when the two compounds are dissolved in different solvents.

Figure 2:
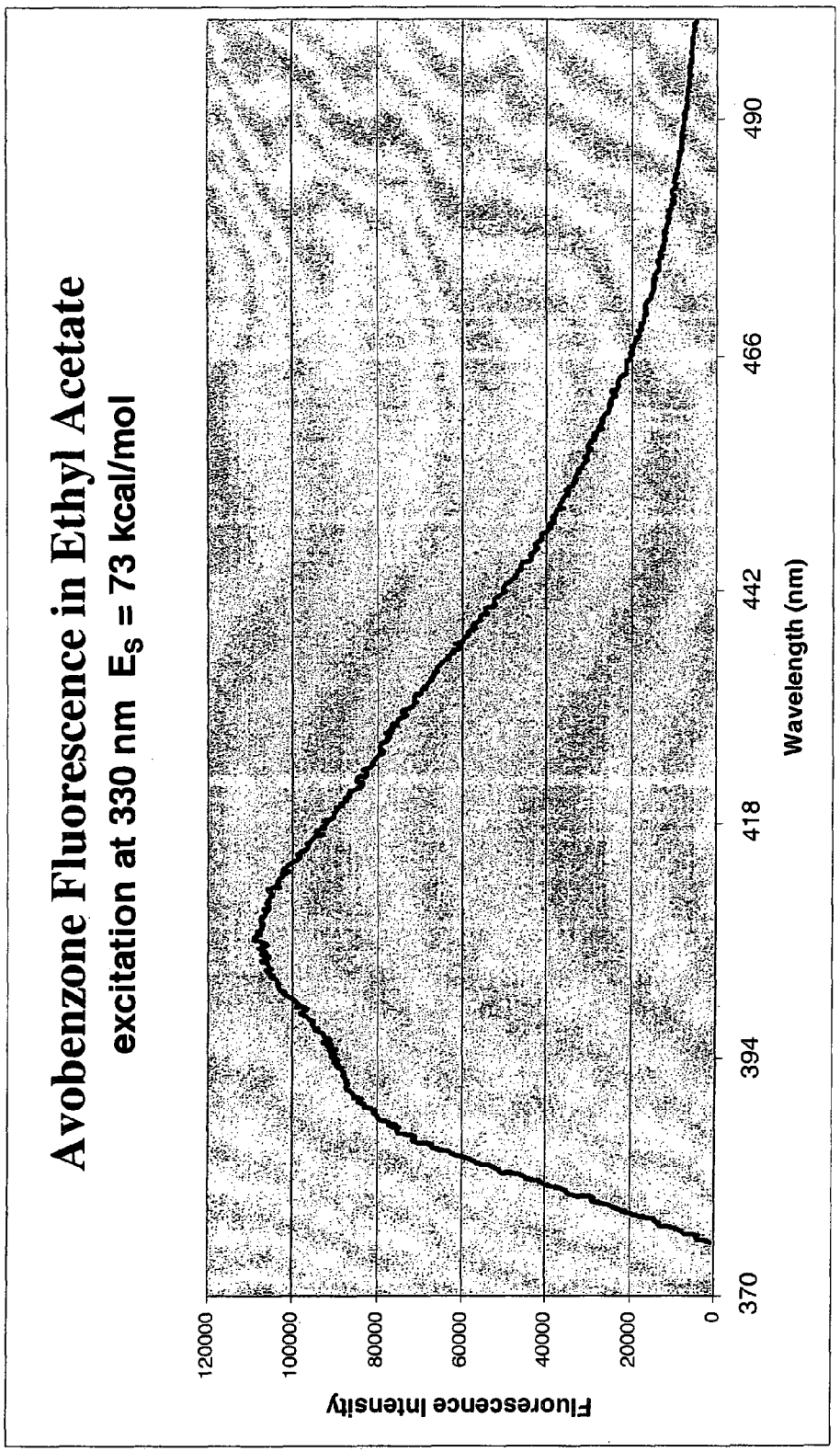
FIG. 2 is a graph of Avobenzone's fluorescence emission in ethyl acetate when excited by UV radiation at 330 nm.
Figure 3:
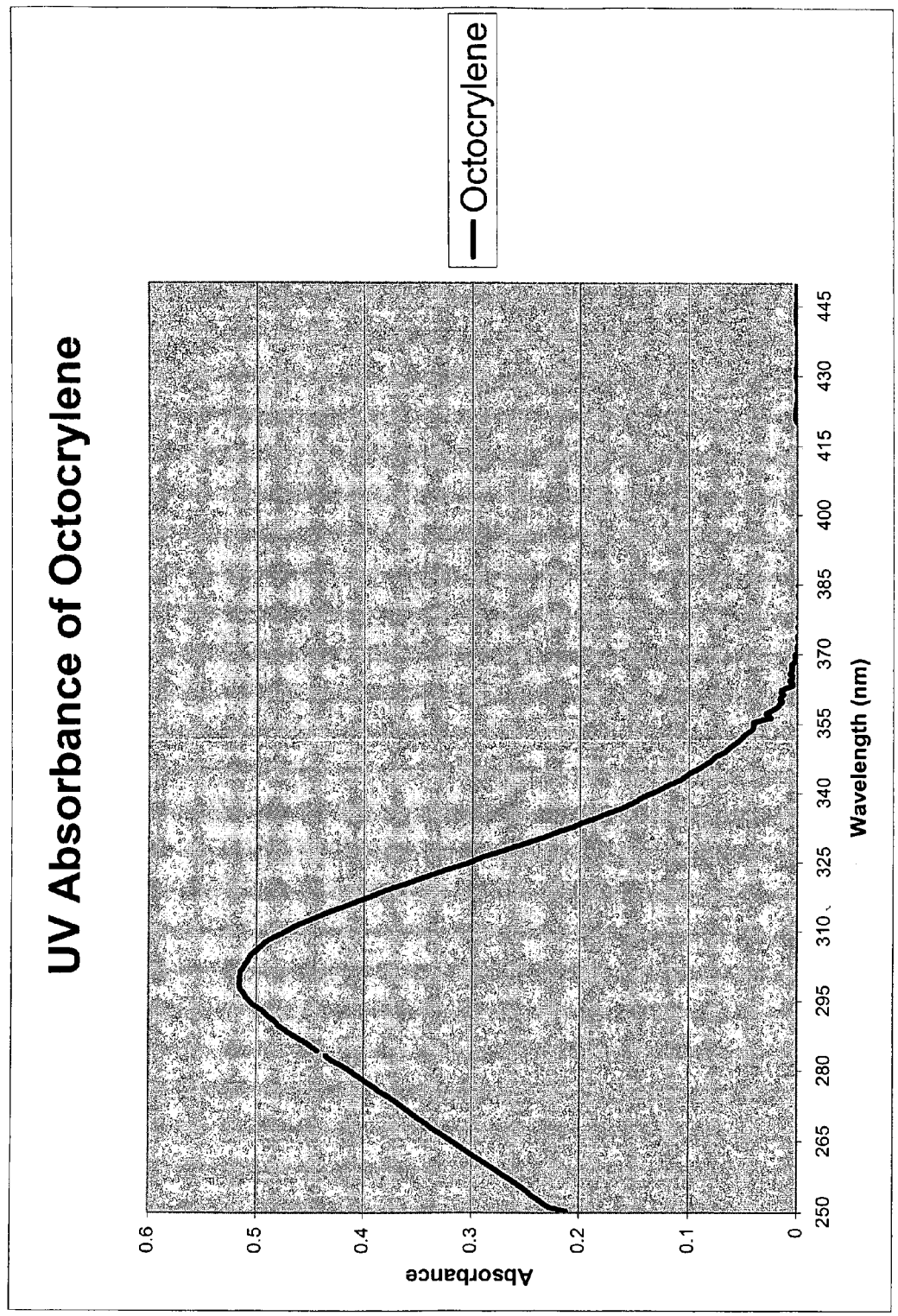
FIG. 3 is a graph of the UV absorbance of Octocrylene at various UV wavelengths.
Figure 4:
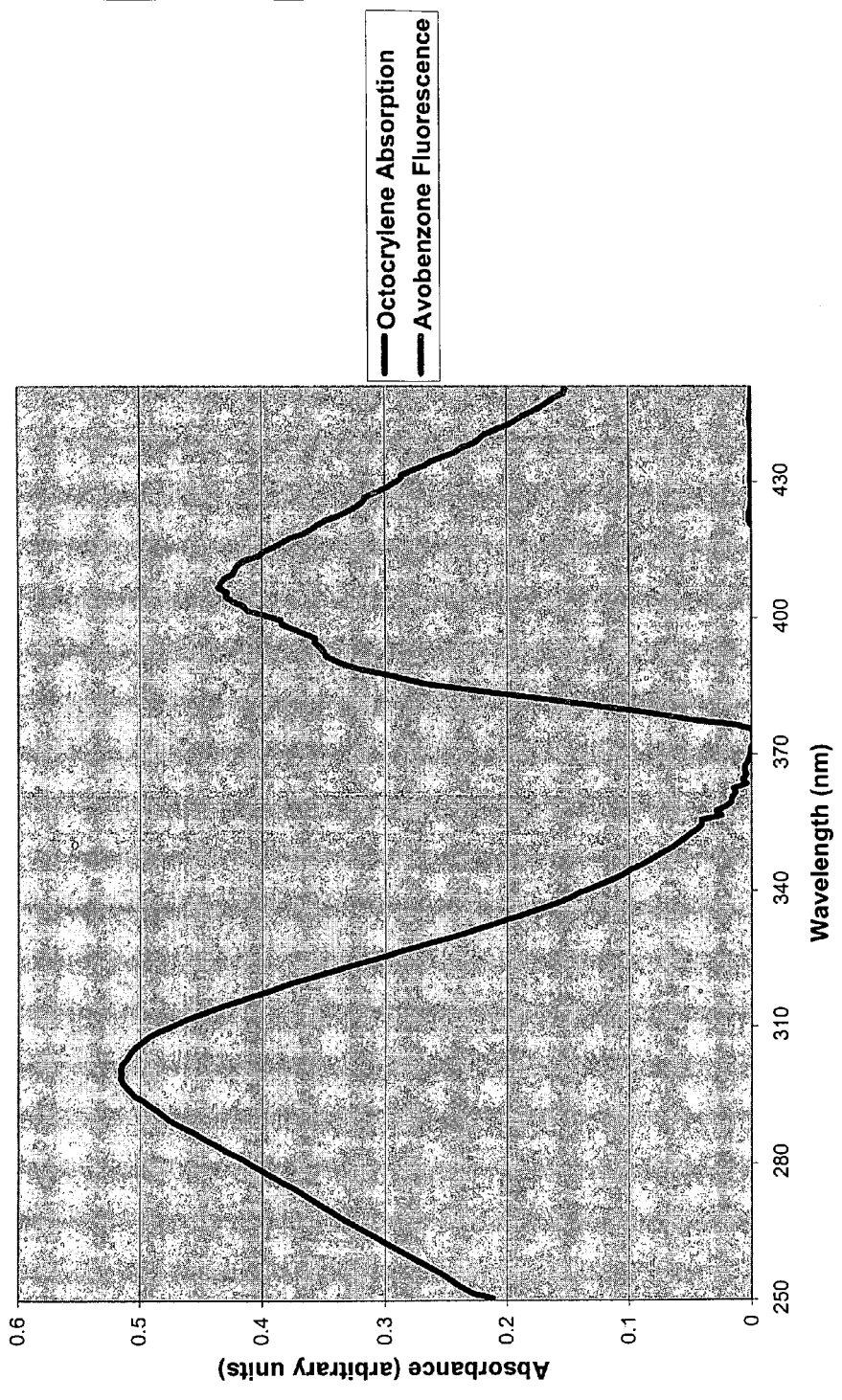
FIG. 4 is a graph showing that there is no spectral overlap between Octocrylene absorption and Avobenzone fluorescence.

For example, FIG. 1 shows the mechanism for octocrylene to accept (quench) the electronic triplet state energy of avobenzone ($E_T$=57 kcal/mol) in the absence of octinoxate; and FIG. 2 is a fluorescence emission spectra of avobenzone in ethyl acetate, having an electronically excited singlet state energy of 73 kcal/mol. FIG. 3 is the fluorescence absorption spectra of octocrylene in ethyl acetate. When FIGS. 2 and 3 are overlapped, keeping the wavelength (nm) x-axes in alignment, there is no overlap between the fluorescence emission spectra of avobenzone and the fluorescence absorption spectra of octocrylene, as shown in FIG. 4. It is predicted, therefore, that octocrylene, cannot quench the electronic singlet state excited energy from avobenzone (avobenzone emits its $E_s$ at $370^+$ nm and octocrylene absorbs (accepts) $E_s$ at less than 370 nm—no singlet state photostabilization). As shown in the lack of decrease of fluorescence of FIG. 6 of avobenzone with and without 1:0.5 and 1:1 weight ratios of avobenzone:octocrylene, octocrylene does not quench the electronic singlet state excited energy from avobenzone.

Figure 5:
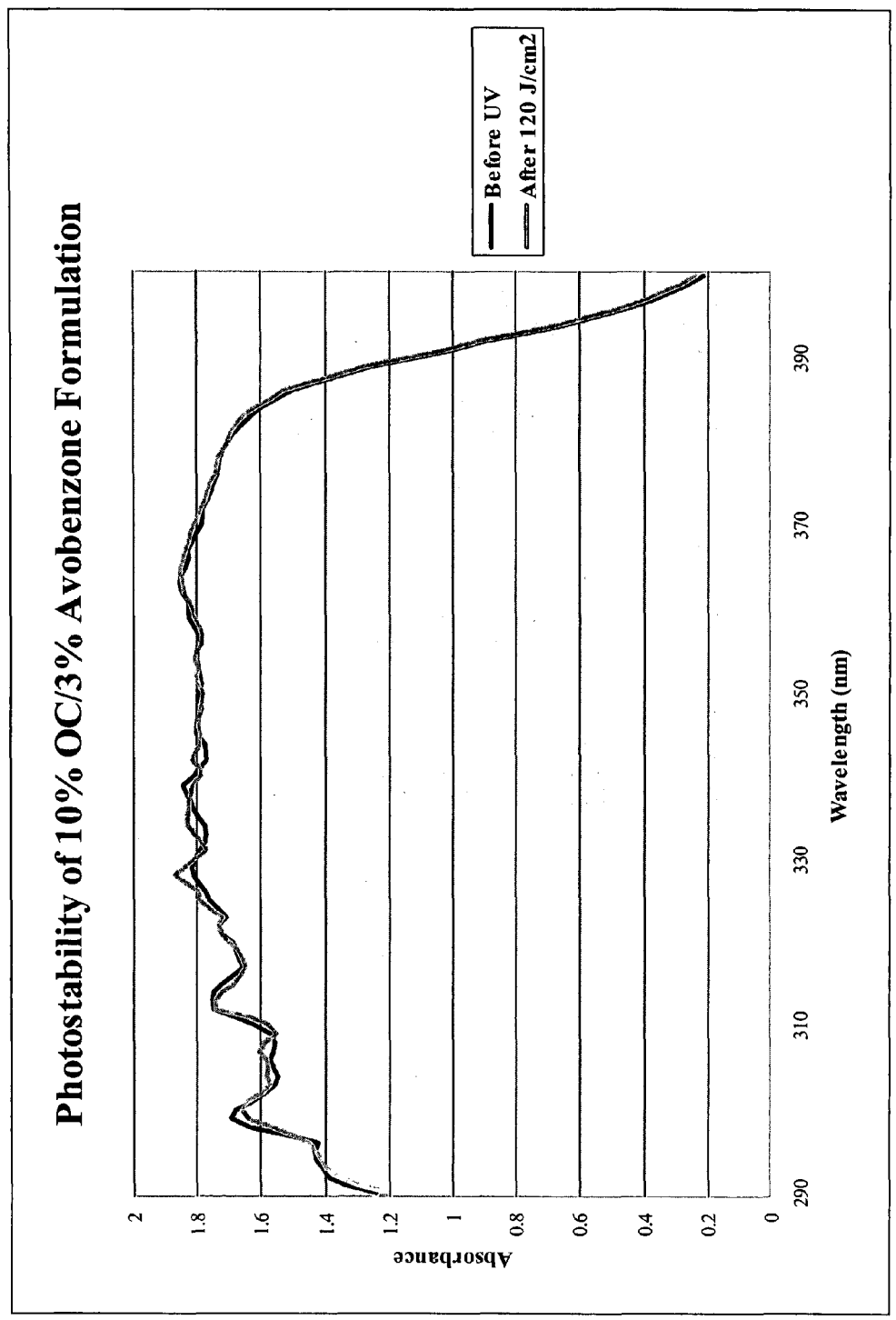
FIG. 5 is a graph showing the photostability of a combination of 10 wt. % Octocrylene and 3 wt. % Avobenzone before and after being subjected to 120 J/cm$^2$ of UV radiation over the wavelengths of 290-400 nm, showing that Octocrylene quenches the excited triplet state energy ($E_T$) from Avobenzone.

Octocrylene, however, does have an electronic triplet state excited energy ($E_T$) of 56 kcal/mol, as shown in FIG. 1, and will accept (quench) the electronic triplet state excited energy from avobenzone, as shown in FIG. 5.

Figure 6:
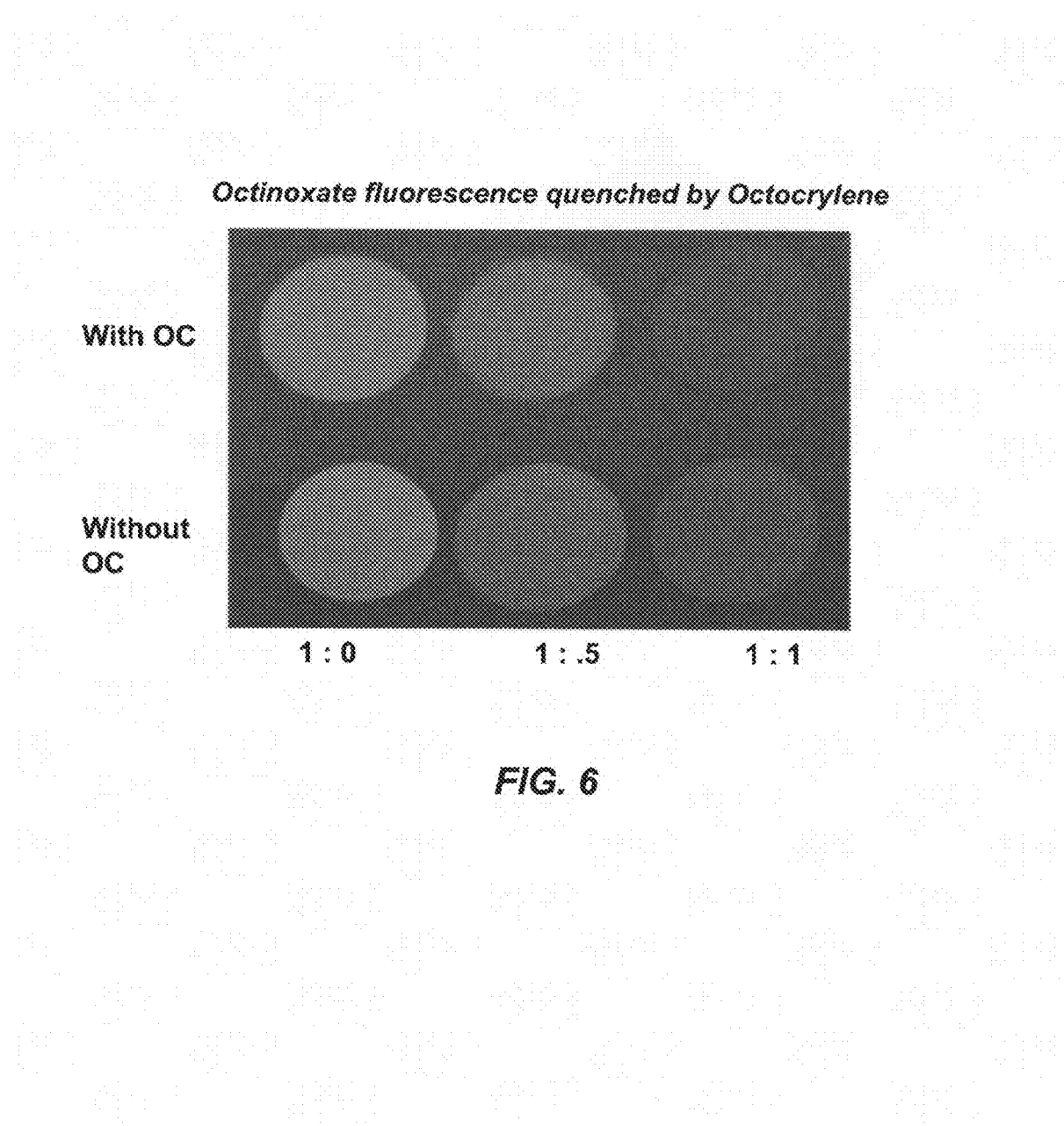
FIG. 6 is a color photo showing essentially no decrease in fluorescence of Avobenzone when combined with Octocrylene, and subjected to long wave UV radiation (peak 365 nm), at weight ratios of Avobenzone:Octocrylene of 1:0.5 and 1:1 indicating that Octocrylene does not accept (quench) the excited singlet state energy from Avobenzone.
Figure 7:
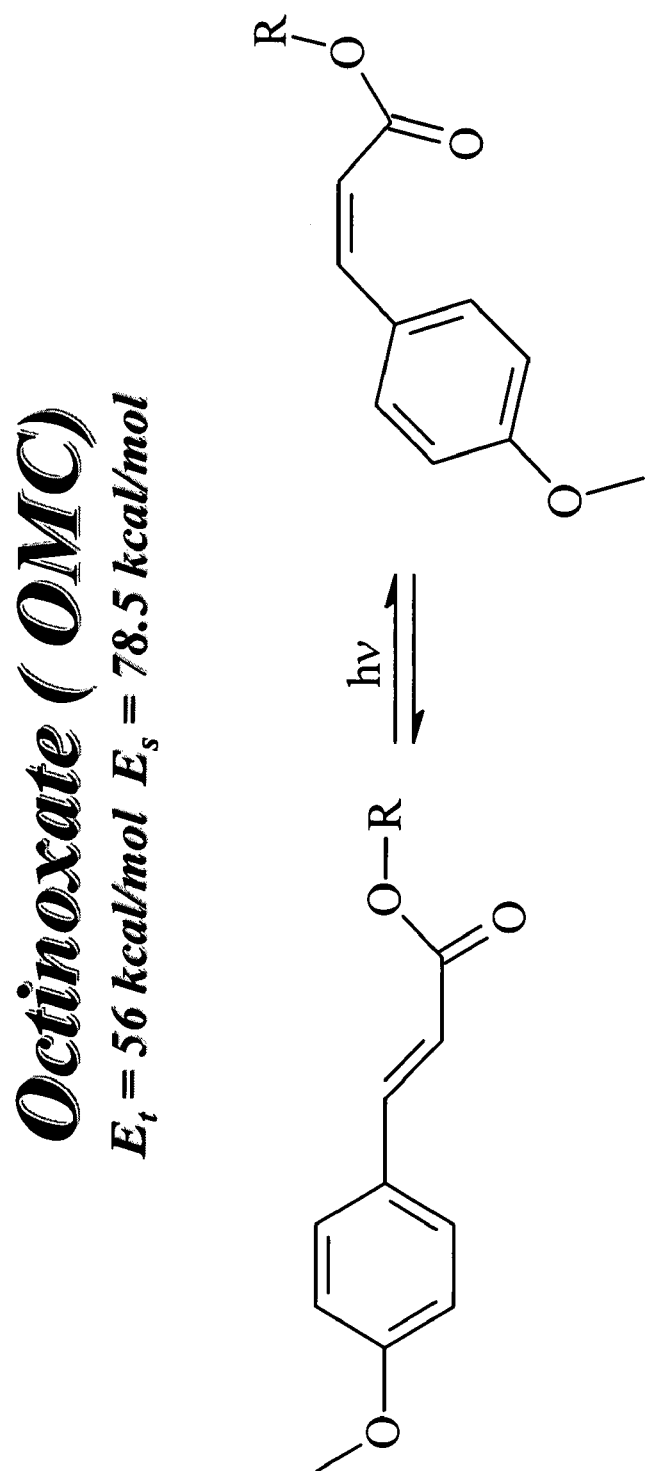
FIG. 7 shows the singlet excited stated ($E_S$) and triplet excited state ($E_T$) energies of Octinoxate (octyl methoxy cinnamate)

The singlet state ($E_S$) and triplet state ($E_T$) excited energies of Octinoxate are shown in FIG. 6.

Figure 8:
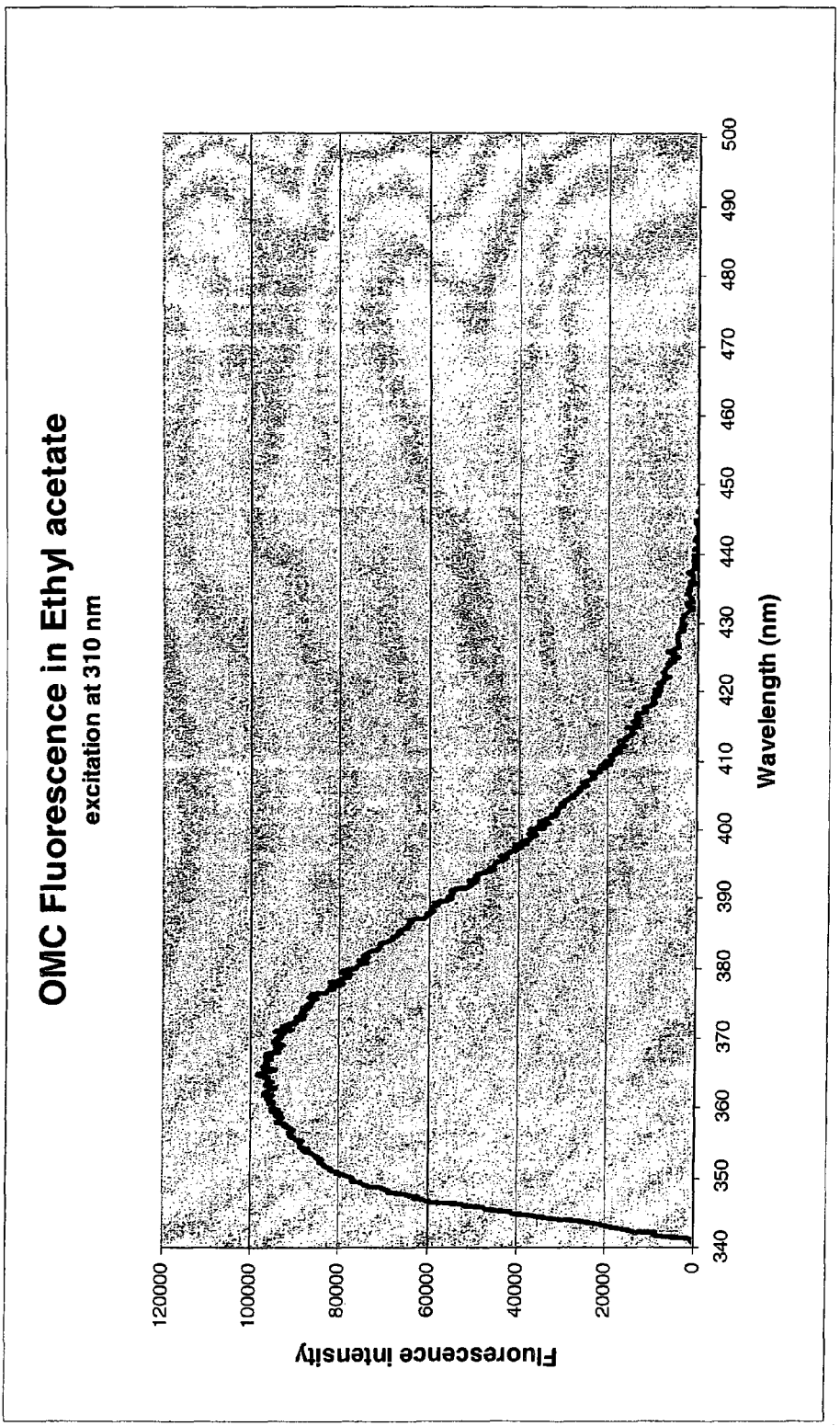
FIG. 8 is a graph of the fluorescence emission of octyl methoxy cinnamate (OMC) in ethyl acetate when excited by UV radiation at 330 nm.
Figure 9:
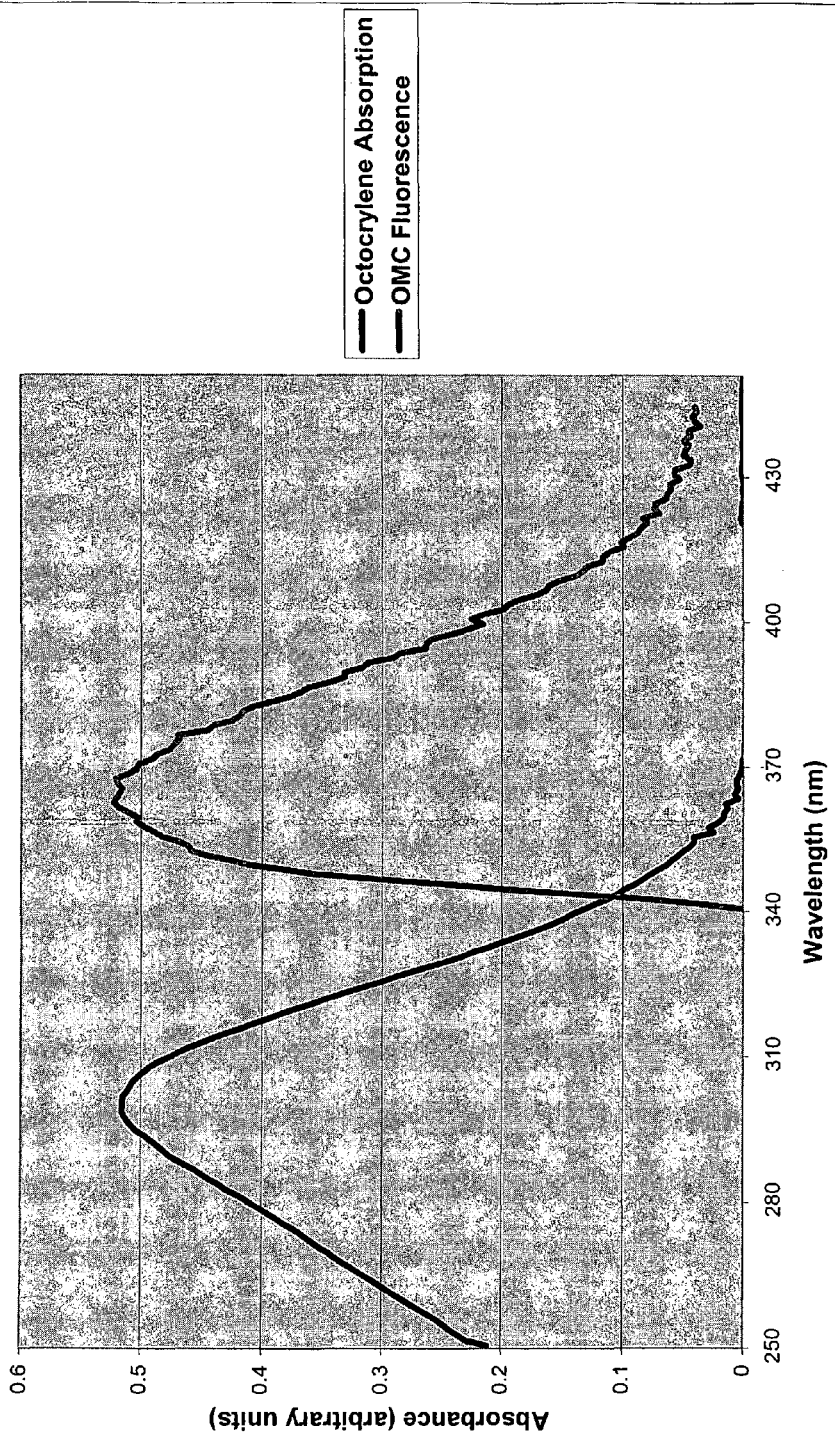
FIG. 9 is a graph showing the spectral overlap between octocrylene absorption and Octinoxate fluorescence.
Figure 10:
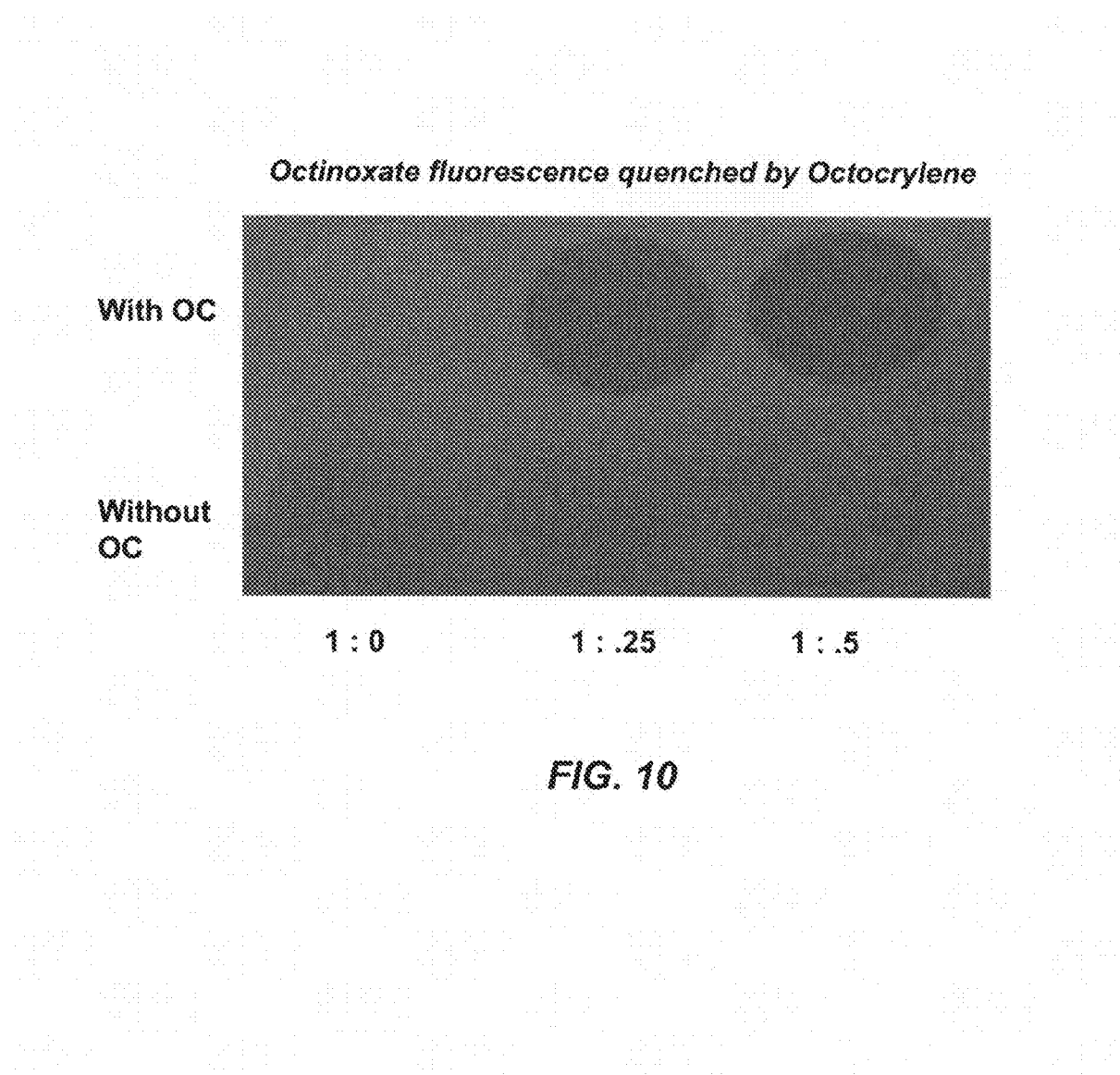
FIG. 10 is a color photo showing the decrease in fluorescence of Octinoxate when combined with Octocrylene (OC), and subjected to long wave UV radiation (peak 365 nm), at weight ratios of Octinoxate:Octocrylene of 1:0.25 and 1:0.50 indicating that Octocrylene accepts (quenches) the excited singlet state energy from Octinoxate.

FIG. 8 is a fluorescence emission spectra for octinoxate in ethyl acetate. Overlapping the absorbance (fluorescence absorption) graph for octocrylene of FIG. 3 and the fluorescence emission graph of FIG. 8 shows spectral overlap between wavelengths of 340 nm and 370 nm (at the peak of the fluorescence emission spectra of the singlet state energy emission of octinoxate). (See FIG. 9) As shown in the substantial decrease in fluorescence (darker circles) of FIG. 10, with increased weight ratios of octocrylene to octinoxate (1:0; 1:0.25 and 1:0.5 octinoxate: octocrylene) the fluorescence is visually seen to decrease. Octocrylene, therefore, quenches the electronic singlet state excited energy from octinoxate, and would therefore be predicted to photostabilize Octinoxate in the presence of a compound, such as Avobenzone, that is known to photochemically react with it.

Figure 11:
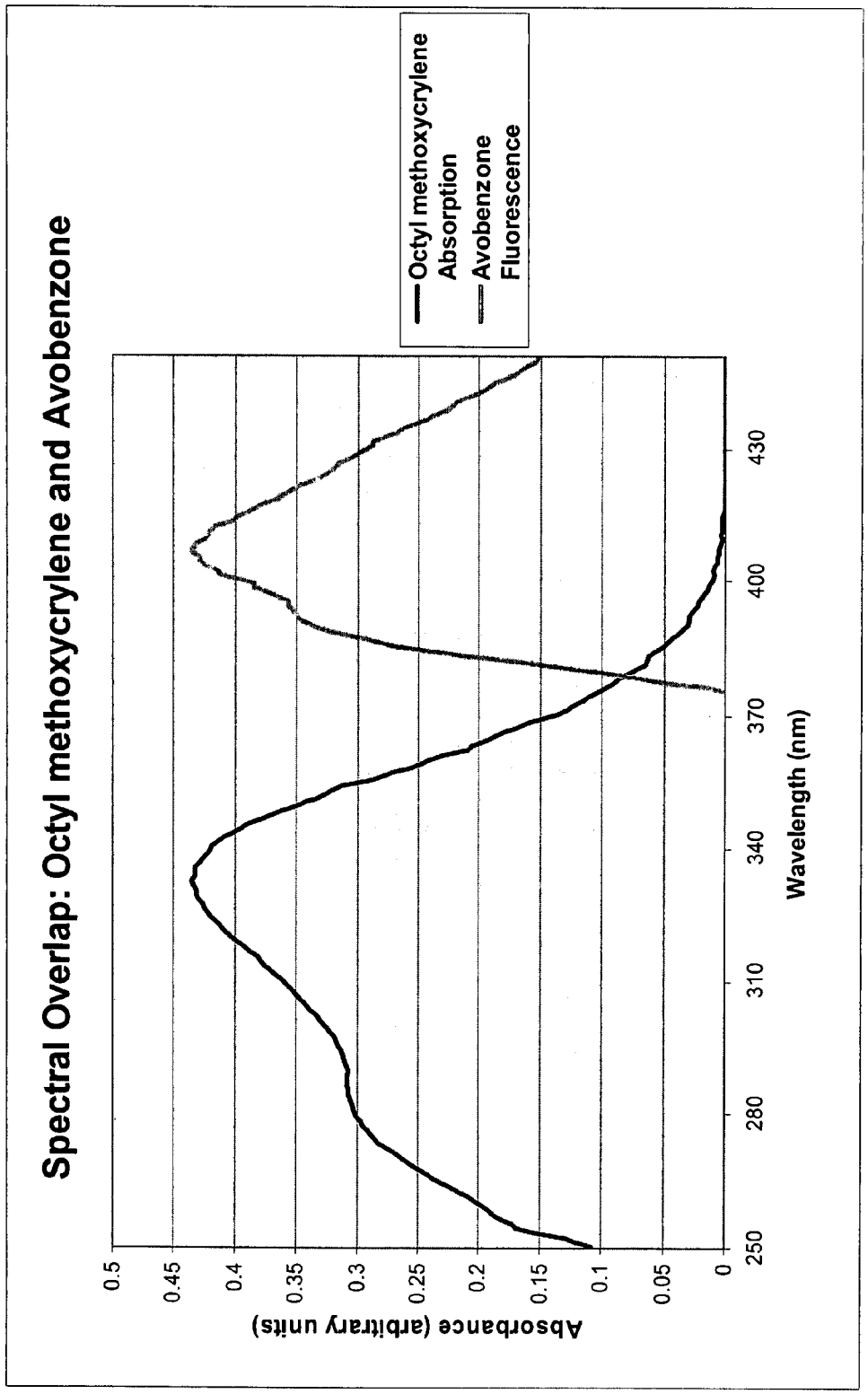
FIG. 11 is a graph showing the spectral overlap between Octyl methoxycrylene absorption and Avobenzone fluorescence.
Figure 12:
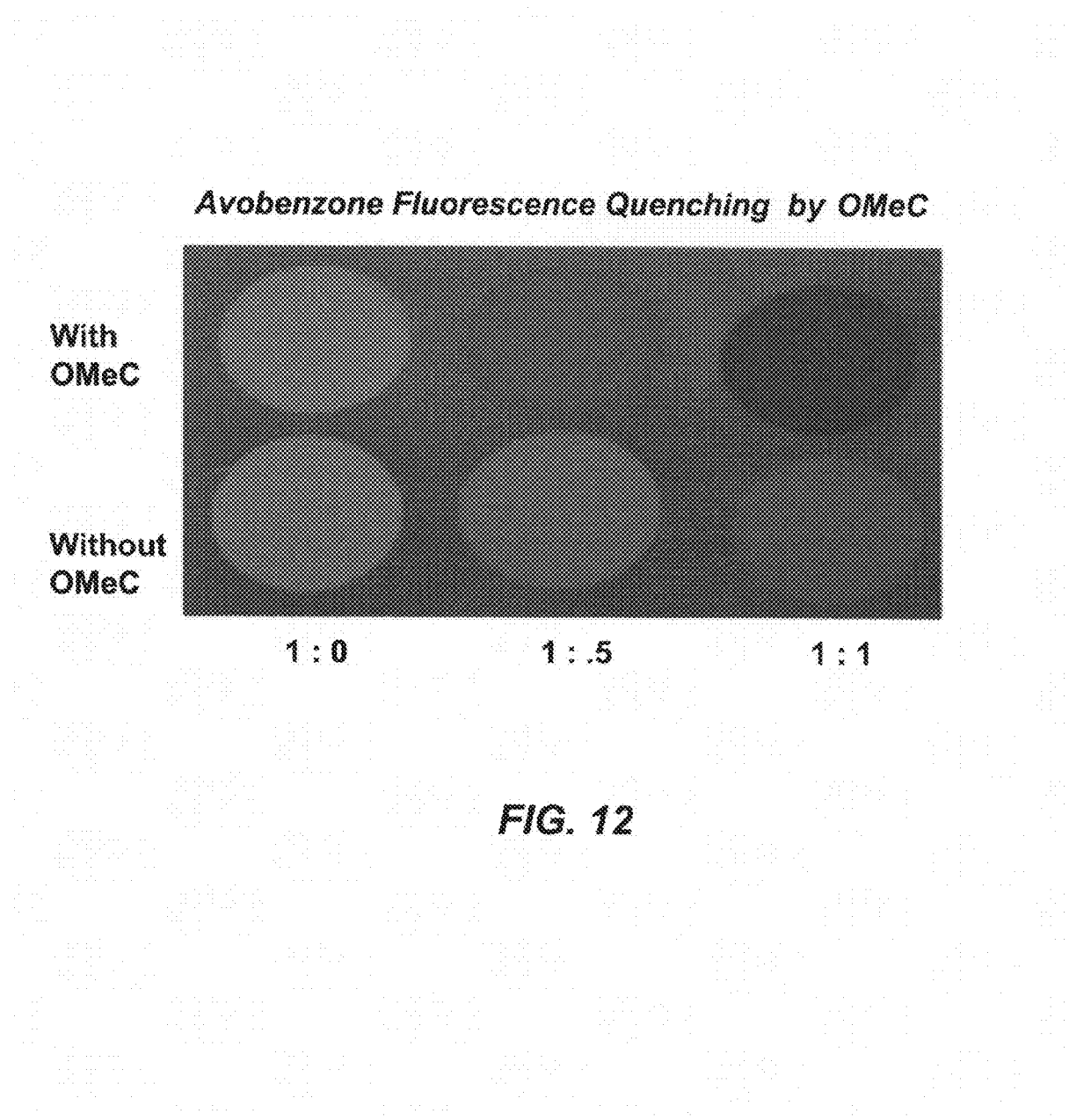
FIG. 12 is a color photo showing the decrease in fluorescence of Avobenzone when combined with octyl methoxycrylene (OMeC), and subjected to long wave UV radiation (peak 365 nm), at weight ratios of Avobenzone:OMeC of 1:0.5 and 1:1 indicating that OMeC accepts (quenches) the excited singlet state energy from Avobenzone.
Figure 13:
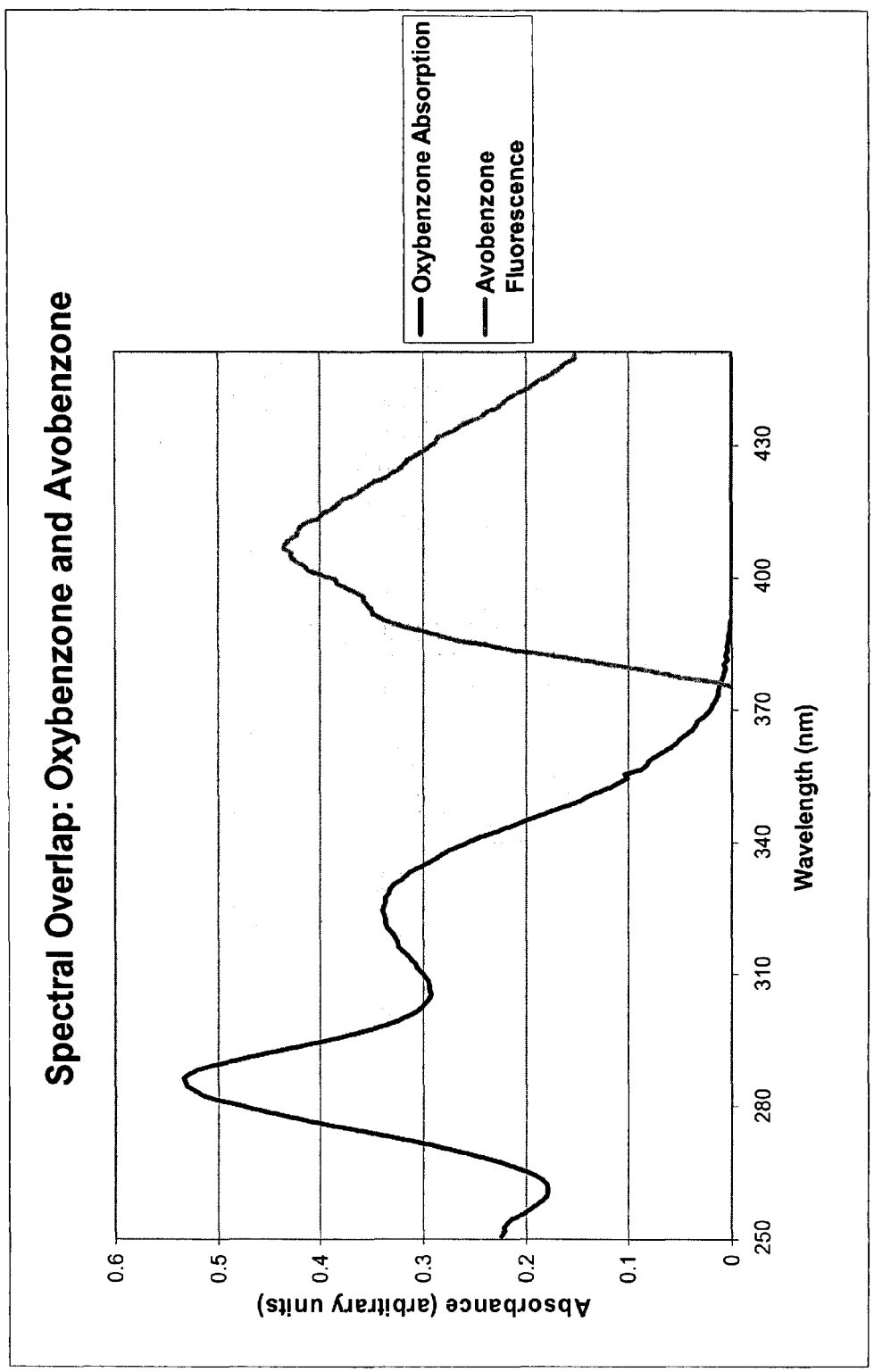
FIG. 13 is a graph showing the spectral overlap between Oxybenzone absorption and Avobenzone fluorescence, predicting that Oxybenzone will exhibit a weak photostabilizing effect on Avobenzone in a sunscreen composition.
Figure 14:
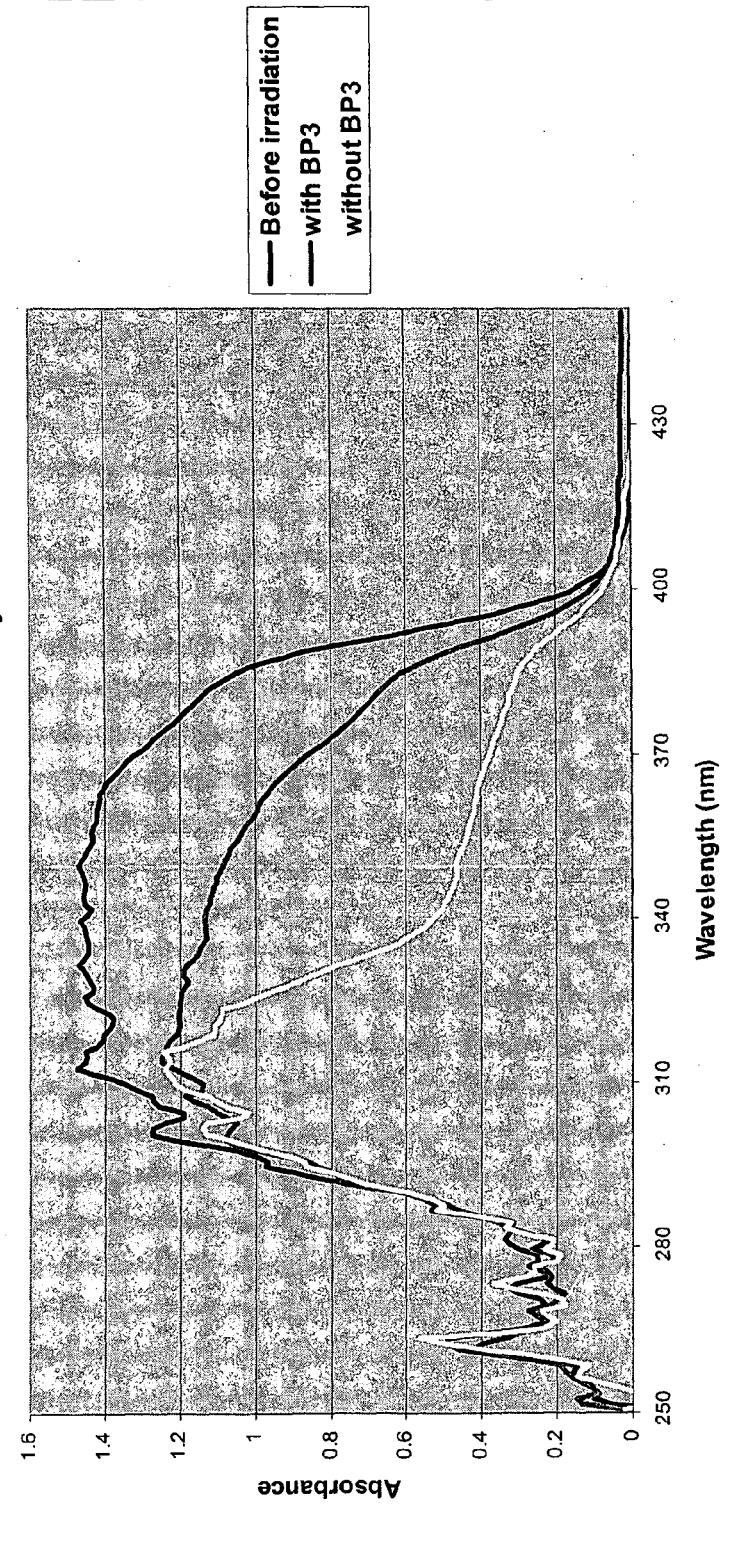
FIG. 14 is a graph that confirms the weak photostabilizing effect by Oxybenzone (BP#) on Avobenzone.

Similarly, good spectral overlap (FIG. 11) is seen in the octyl methoxycrylene (OMeC) absorption spectra and avobenzone emission spectra (FIG. 2) resulting in the fluorescence lessening of FIG. 12 (increased darkening of observed fluorescence in a dark room (or read by machine) is observed in FIG. 12 with the addition of more OMeC from weight ratios of 1:0, 1:0.5, and 1:1 (avobenzone:OMeC). The methoxycrylene molecule, therefore, photostablizes avobenzone by accepting (quenching) its electronic singlet state excited energy. By accepting the singlet state excited energy, the avobenzone molecule has no opportunity to reach its triplet state excited energy, or to be destroyed by photochemical reaction, as shown in the schematic DEXSTER, © 2007 The HallStar Company (FIG. 15 graph).

Figure 15:
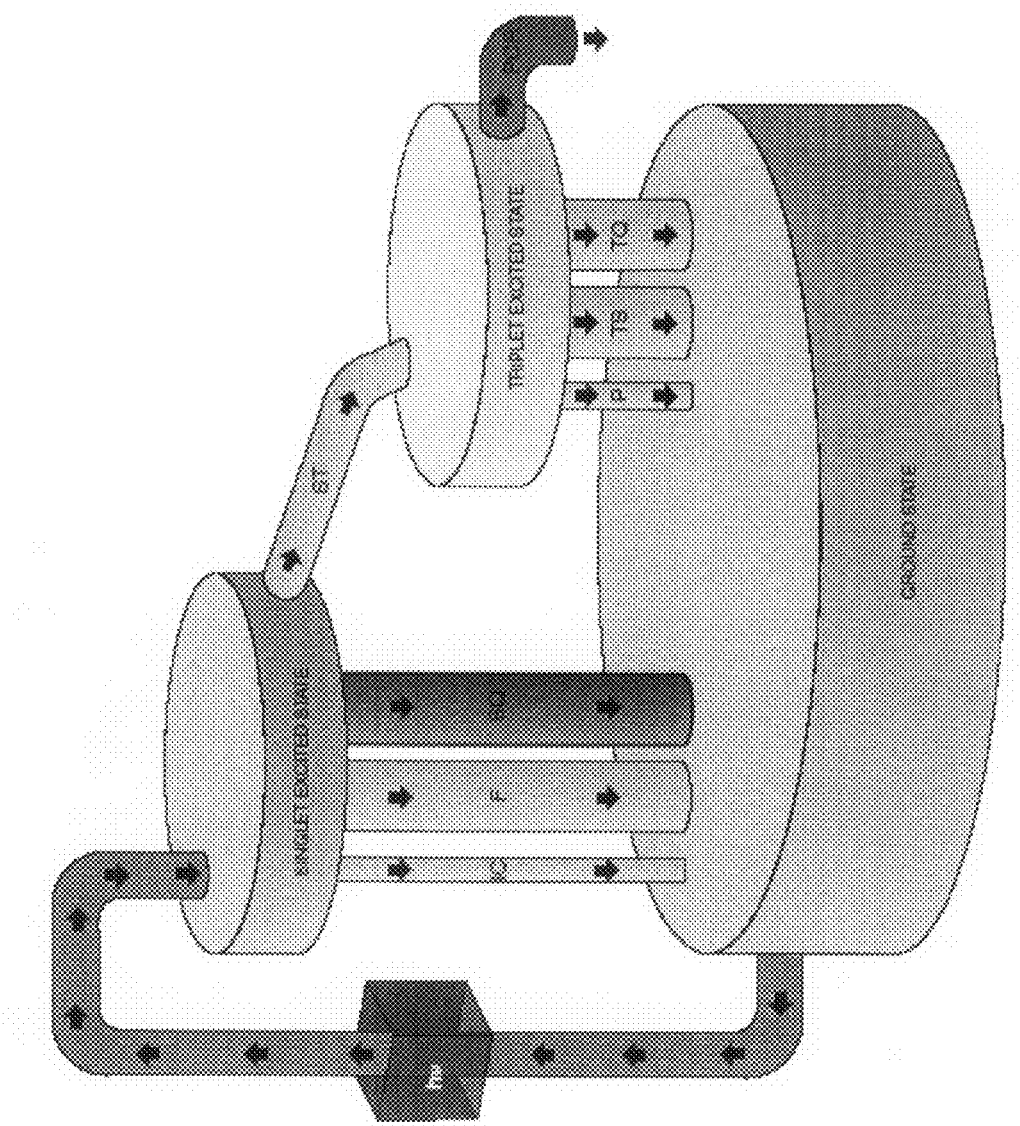
FIG. 15 is a graphical depiction of the processes by which UV filters dissipate their excited state energy and return to ground state.

DEXSTER, © 2007 The HallStar Company, schematic of FIG. 15 is an acronym for Deactivation of Excited States by Emissions and Radiationless pathways, and is a graphical depiction of the processes by which UV filters dissipate their excited state energy and return to the ground state. The circular structures are reservoirs that contain all the UV filter molecules in their various states: ground (non-excited); singlet (excited); and triplet (excited).

The energy in UV radiation pumps molecules from the ground state reservoir upwardly through the far left conduit to the singlet excited state reservoir.

The conduits of FIG. 15 having downwardly pointing arrows (P, TS and TQ) "drain" the excited state molecules directly to the ground state reservoir. The excited molecules also may be drained from the singlet excited state to the triplet excited state (see ST conduit of FIG. 15) or directly to the ground state (see IC, F, and SQ).

IC=Internal Conversion
F=Fluorescence
SQ=Singlet Quenching
ST=Singlet to Triplet Intersystem Crossing
P=Phosphorescence
TS=Triplet to Singlet (Ground) Intersystem Crossing
TQ=Triplet Quenching
PCR=Photochemical Reactions The PCR faucet of FIG. 15 "leaks" all the molecules that are "destroyed" by photochemical reactions.

The invention claimed is:

1. A method of visually testing a compound for its capability of quenching singlet excited state energy from a photon-excited, photodegradable photoactive compound, comprising:

dissolving a photoactive compound in a solvent to form a composition (1), applying composition (1) onto a TLC plate, and exposing the composition (1) to UV radiation in an amount sufficient for the photoactive compound to reach an electronic singlet excited state and fluoresce;

visually observing a degree of fluorescence of composition (1) in a dark environment;

dissolving said photoactive compound and a test compound in a solvent to form a mixture (2), applying mixture (2) onto a TLC plate, and exposing the mixture (2) to UV radiation to the same degree as composition (1);

visually observing a degree of fluorescence of mixture (2) in a dark environment;

and visually comparing the degree of fluorescence of composition (1) with the degree of fluorescence of mixture (2) to determine if there is a difference in the degree of fluorescence.

2. The method of claim 1, wherein the TLC plate is silica gel coated.

3. The method of claim 1, wherein the solvent of composition (1) is the same as the solvent in composition (2).

4. The method of claim 1, wherein the photoactive compound is selected from the group consisting of p-aminobenzoic acid and salts and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dihydroxy-naphthoic acid and salts thereof; o-hydroxydiphenyldisulfonate and salts and derivatives thereof; p-hydroxdydiphenyldisulfonate and salts and derivatives thereof; coumarin and derivatives thereof; diazole derivatives; quinine derivatives and salts thereof; quinoline derivatives; naphthalates and salts thereof, dibenzoylmethane and derivatives thereof; and combinations of the foregoing.

5. The method of claim 1, wherein the photoactive compound comprises a dibenzoylmethane derivative.

6. The method of claim 5, wherein the photoactive compound comprises a dibenzoylmethane derivative selected from the group consisting of 2-methyldibenzoylmethane; 4-methyldibenzoylmethane; 4-isopropyldibenzoylmethane; 4-tert-butyldibenzoylmethane; 2,4-dimethydibenzoylmethane; 2-5-dimethydibenzoylmethane; 4,4-diispropyldibenzoylmethane; 4,4-dimethoxydibenzoylmethane; 4-tert-butyl-4-methoxdibenzoylmethane; 2-methyl-5-isopropy-4-methoxydibenzoylmethane; 2-methyl-5-tert-butyl-4-methoxydibenzoylmethane; 2,4-dimethyl-4-methoxydibenzoymethane; 2,6-dimethyl-4-tert-butyl-4-methoxydibenzolmethane, and combinations thereof.

7. The method of claim 4, wherein the photoactive compound comprises a derivative of cinnamic acid.

8. The method of claim 7, wherein the photoactive compound comprises 2-ethylhexyl-p-methoxycinnamate.

9. The method of claim 1, wherein the composition (1) and the mixture (2) each includes a diester or polyester of naphthalene dicarboxylic acid selected from the group consisting of compounds of formula (II) and (III), and combinations thereof:

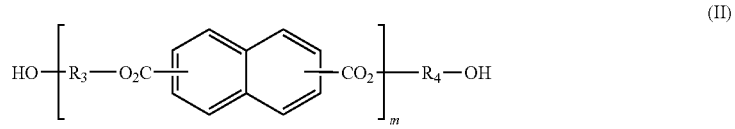

(II)

-continued

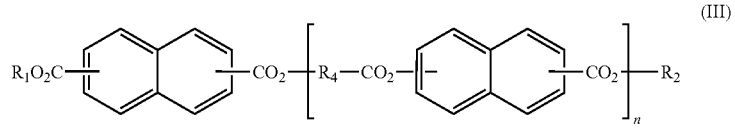
(III)

wherein $R_1$ and $R_2$ are the same or different and selected from the group consisting of $C_1$-$C_{22}$ alkyl groups, diols having the structure HO—$R_4$—OH, and polyglycols having the structure HO—$R_3$—(—O—$R_4$-)n-OH; wherein each $R_3$ and $R_4$ is the same or different and selected from the group consisting of $C_1$-$C_6$ straight or branched chain alkyl groups; and wherein m and n are each in a range of 1 to 100.

10. A method of machine testing a compound for its capability of quenching singlet excited state energy from a photon-excited photoactive compound comprising:
dissolving a photoactive, photodegradable compound in a solvent to form a composition (1), applying composition (1) onto a TLC plate, and exposing composition (1) to UV radiation in an amount sufficient for the photoactive compound to reach an electronic singlet excited state and fluoresce;
machine quantitizing the fluorescence of composition (1);
dissolving said photoactive compound and a test compound in a solvent to form a mixture (2), applying composition (1) onto a TLC plate, and exposing the mixture (2) to UV radiation to the same degree as composition (1);
machine quantitizing the fluorescence of composition (2); and
comparing the fluorescence quantity of mixture (2) to the fluorescence quantity of composition (1) to determine if there is a machine quantitized difference in fluorescence.

11. The method of claim 10, wherein the composition (1) and mixture (2) are applied to a TLC plate is silica gel coated plate prior to exposing composition (1) and mixture (2) to said UV radiation.

12. The method of claim 10, wherein the solvent of composition (1) is the same as the solvent in composition (2).

13. The method of claim 10, wherein the photoactive compound is selected from the group consisting of p-aminobenzoic acid and salts and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dihydroxy-naphthoic acid and salts thereof; o-hydroxydiphenyldisulfonate and salts and derivatives thereof; p-hydroxdydiphenyldisulfonate and salts and derivatives thereof; coumarin and derivatives thereof; diazole derivatives; quinine derivatives and salts thereof; quinoline derivatives; naphthalates and salts thereof, dibenzoylmethane and derivatives thereof; and combinations of the foregoing.

14. The method of claim 13, wherein the photoactive compound comprises a dibenzoylmethane derivative selected from the group consisting of 2-methyldibenzoylmethane; 4-methyldibenzoylmethane; 4-isopropyldibenzoylmethane; 4-tert-butyldibenzoylmethane; 2,4-dimethydibenzoylmethane; 2-5-dimethydibenzoylmethane; 4,4-diispropyldibenzoylmethane; 4,4-dimethoxydibenzoylmethane; 4-tert-butyl-4-methoxdibenzoylmethane; 2-methyl-5-isopropy-4-methoxydibenzoylmethane; 2-methyl-5-tert-butyl-4-methoxydibenzoylmethane; 2,4-dimethyl-4-methoxydibenzoymethane; 2,6-dimethyl-4-tert-butyl-4-methoxydibenzolmthane, and combinations thereof.

15. The method of claim 10, wherein the photoactive compound comprises a derivative of cinnamic acid.

16. The method of claim 15, wherein the photoactive compound comprises 2-ethylhexyl-p-methoxycinnamate.

17. The method of claim 1 further including the step of allowing composition (1) and mixture (2) to dry for at least 5 minutes on the TLC plate prior to exposing composition (1) and mixture (2) to UV radiation sufficient to cause composition (1) and mixture (2) to fluoresce.

18. The method of claim 10 further including the step of allowing composition (1) and mixture (2) to dry for at least 5 minutes on the TLC plate prior to exposing composition (1) and mixture (2) to UV radiation sufficient to cause composition (1) and mixture (2) to fluoresce.

* * * * *

UNITED STATES PATENT AND TRADEMARK OFFICE
CERTIFICATE OF CORRECTION

| | |
|---|---|
| PATENT NO. | : 7,776,614 B2 |
| APPLICATION NO. | : 11/891280 |
| DATED | : August 17, 2010 |
| INVENTOR(S) | : Bonda |

It is certified that error appears in the above-identified patent and that said Letters Patent is hereby corrected as shown below:

Page 1 of 2

In the Claims:

At Column 10, line 31, "hydroxdydiphenyldisulfonate" should be -- hydroxydiphenyldisulfonate --.

At Column 10, lines 42-43, "2,4-dimethydibenzoylmethane" should be -- 2,4-dimethyldibenzoylmethane --.

At Column 10, line 43, "2-5-dimethydibenzoylmethane" should be -- 2-5-dimethyldibenzoylmethane --.

At Column 10, line 45, "methoxdibenzoylmethane" should be -- methoxydibenzoylmethane --.

At Column 10, lines 45-46, "isopropy" should be -- isopropyl --.

At Column 10, lines 47-48, "methoxydibenzoymethane" should be -- methoxydibenzoylmethane --.

At Column 10, line 49, "methoxydibenzolmethane" should be -- methoxydibenzoylmethane --.

At Column 12, line 14, "hydroxdydiphenyldisulfonate" should be -- hydroxydiphenyldisulfonate --.

At Column 12, lines 23-24, "2,4-dimethydibenoylmethane" should be -- 2,4-dimethyldibenzoylmethane --.

Signed and Sealed this
Fourteenth Day of June, 2011

David J. Kappos
*Director of the United States Patent and Trademark Office*

At Column 12, line 24, "2-5-dimethydibenzoylmethane" should be
-- 2-5-dimethyldibenzoylmethane --.

At Column 12, line 27, "methoxdibenzoylmethane" should be
-- methoxydibenzoylmethane --.

At Column 12, lines 27-28, "isopropy" should be -- isopropyl --.

At Column 12, line 29, "methoxydibenzoymethane" should be
-- methoxydibenzoylmethane --.

At Column 12, line 30, "methoxydibenzolmthane" should be -- methoxydibenzoylmethane --.